United States Patent [19]

Lavigne

[11] 4,057,062
[45] Nov. 8, 1977

[54] URINARY DEVICE

[76] Inventor: Geraldine Lavigne, 333 Farview Road, Victoria, British Columbia, Canada, V9C1V7

[21] Appl. No.: 655,706

[22] Filed: Feb. 6, 1976

[51] Int. Cl.² .............................................. A61F 5/44
[52] U.S. Cl. ..................... 128/295; 128/2 F; 128/350 R
[58] Field of Search ................... 4/110; 128/DIG. 24, 128/294, 295, 2 F, 348–350, 350 R; 15/315; 285/226, 260, 319, 299–303

[56] References Cited

U.S. PATENT DOCUMENTS

| 228,883 | 6/1880 | Freeman | 285/303 |
| 3,261,107 | 7/1966 | Ponczek et al. | 15/315 |
| 3,742,953 | 7/1973 | Lee | 128/295 |

Primary Examiner—John D. Yasko
Assistant Examiner—Henry S. Layton
Attorney, Agent, or Firm—Lawrence Preska

[57] ABSTRACT

A urinary device that includes an elongated length of flexible and telescopical tubing adapted to communicate between the collection bag and the body.

8 Claims, 2 Drawing Figures

URINARY DEVICE

BACKGROUND OF THE INVENTION

This invention relates to urinary drainage devices, more particularly, to a new tubing for use therein.

The prior art teaches a variety of urinary drainage devices, for example those disclosed in U.S. Pat. Nos. 3,356,091; 3,421,504; 3,421,507; 3,511,241; 3,683,930; 3,721,243; 3,742,953; 3,781,922; 3,835,857; and many others. All of the foregoing are deficient, however, in that the length of the tubing is fixed and therefore cannot be easily modified for various physical and logistical situations that may arise; for example, where the patient is standing, sitting, confined in a wheelchair, lying down, etc. There is not one universally acceptable apparatus that may be employed irrespective of the physical position of the patient.

SUMMARY OF THE INVENTION

It is accordingly an object of the instant invention to provide for a new and improved urinary drainage device.

It is another object to provide for one that may be employed in substantially any physical position that the patient is in.

It is a further object to provide for the same at relatively little cost thereby making it generally available.

It is yet another object to provide for a device that may be employed in conjunction with most conventionally used catheters and urine receiving bags.

These and other objects and advantages of the invention will become more apparent from the following detailed disclosure and claims and by reference to the accompanying drawings, in which:

Figure 1:
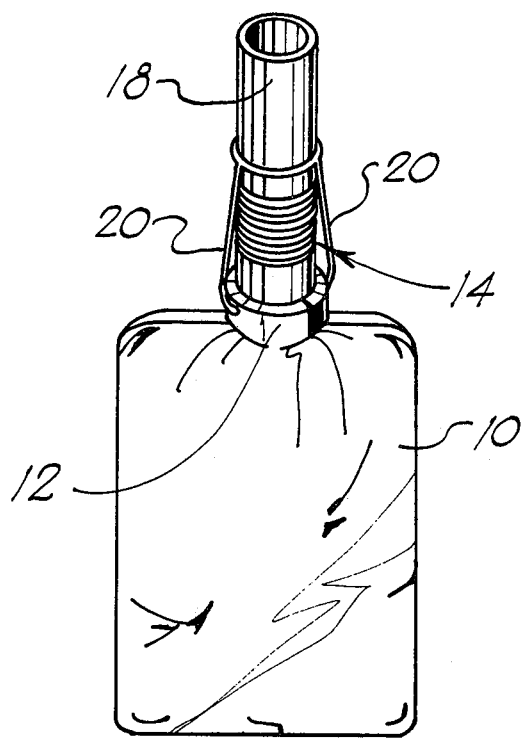
FIG. 1 is a collapsed perspective view.
Figure 2:
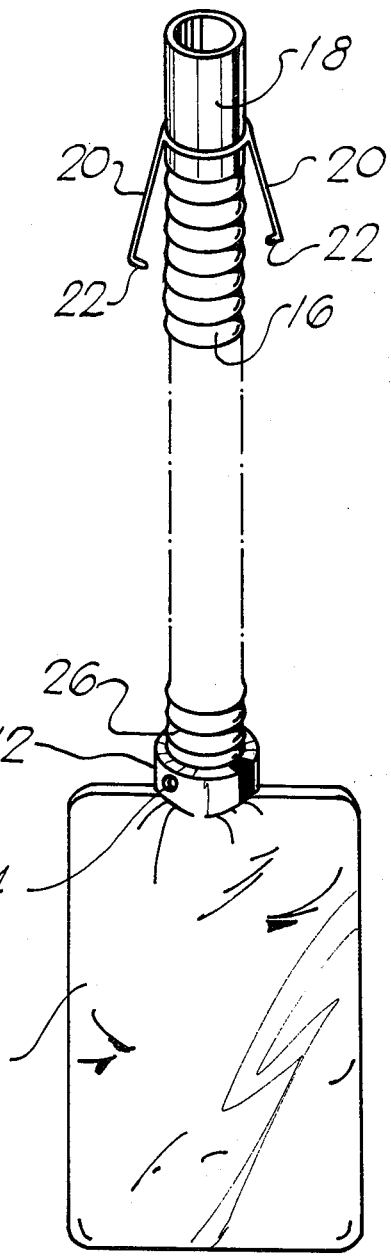
FIG. 2 is an extended perspective view.

Broadly speaking, the instant invention includes the provision of a device especially adapted to be employed in conjunction with a container for the collection of urine, comprising an elongated, flexible, hollow collapsable conduit member, the member including a plurality of continuous telescopic members, the conduit member having two distal ends, one end of the conduit member including a first annular walled hollow collar, the collar defining at least two recesses on the wall, the collar including internal thread means, the thread means adapted to engage external thread means of the container, the other distal end including a second hollow collar, the second collar adapted to receive the urine and including a pair of externally projecting arms, the arms having an end portion out of planar alignment with the remainder of the arm, the end portion adapted to engage the recesses when the conduit member is in the collapsed position and thereby maintain the same, the end portions further adapted to engage a single telescopic member whereby the length of the conduit member is adjusted.

DETAILED DISCLOSURE

Referring more particularly to the drawings there is shown a urine collection bag, container, receptacle 10 or the like that is conventionally employed to receive the urine. In most instances the container 10 will include a screw cap or the like that is adapted to fit over or within a collar 12 defining the mouth of the container 10. The collar 12 can be externally or internally threaded. The instant device includes an elongated length of flexible hollow tubing 14 that defines a plurality of telescopic members 16. In the extended position the same is about 60 inches in length, whereas when collapsed about 6 inches. The tubing 14 is made of any suitable non-toxic, non-allergenic, liquid imperforate material such as plastic or the like that is generally cylindrical in cross section. One distal end of the tubing 14 will include a hollow, substantially rigid collar 18 that is integral therewith and allows the urine to pass from the means that the collar 18 is connected to, through the tubing 14 and into the container 10. The collar 18 will include at least two members 20 that are laterally projecting arms or wings. The members 20 will be integrally joined to the collar 18 such as at the base thereof and be adapted to extend downward therefrom in substantial longitudinal alignment with the tubing 14. The members 20 will also be flexible, but preferably semi-rigid. They are each adapted to pivot slightly at their point of connection to the collar 18. Each member 20 will include a tab portion 22 at its other distal end, i.e., the end opposite the collar 18. The tab portion 22 or clamp arm will preferably be disposed at an angle of about 90° relative to the member 18; i.e., an L shaped configuration.

The tubing 14 will be joined to the collar 18 by any suitable means, i.e., male-female engagement by screw fittings, frictionally engaged, adhesively secured, fused, welded, etc.

In one embodiment of the invention, the same includes the bottle 10 which will be fitted with a collar 12 that defines a pair of recesses 24 disposed thereon that are adapted to receive the tabs 22 when the tubing 14 is in the collapsed position, thereby maintaining the entire unit. The collar 12 may alternatively be an internally threaded member that is unitary with the tubing 14 and adapted to engage the external threads of a conventional screw-cap container.

It should be noted that the tabs 22 are adapted to engage the annular ring sections 26 of each of the members 16 of the tubing 14 such that the length of the tubing 14 may be adjusted for any particular use. Adjustment being possible between several positions of fully extended where the tabs 22 are free and non engaged and multiple positions of engagement wherein the tab 22 engages one of the many rings 26 or the recesses 24, the latter preferably being 180° apart.

The collar 18 will generally communicate with some means that are in direct communication with the urinary organ. It is also possible, however, that the collar 18 may communicate directly with the organ, such as where the collar 18 is formed of a suitable flexible material that will accomate insertion of the organ therein.

Since it is obvious that numerous changes and modifications can be made in the above-described details without departing from the spirit and nature of the invention, it is to be understood that all such changes and modifications are included within the scope of the invention.

I claim:

1. A device especially adapted to be employed in conjunction with a container for the collection of urine, comprising an elongated, flexible, hollow collapsable conduit member, said member including a plurality of continuous telescopic members, each having an annular ring, said conduit member having two distal ends, one end of said conduit member including a first annular walled hollow collar, said collar defining at least two recesses on said wall, said collar including internal thread means, said thread means adapted to engage external thread means of said container, said other distal end including a second hollow collar, said second collar adapted to receive the urine and including a pair of externally projecting arms, said arms having an end portion out of planar alignment with the remainder of said arm, said end portion adapted to engage said recesses when said conduit member is in the collapsed position and thereby maintain the same, said end portions further adapted to engage said annular ring of a single telescopic member whereby the length of said conduit member is adjusted.

2. The device as defined in claim 1 wherein said conduit member has a circular cross section.

3. The device as defined in claim 1 wherein said second collar and said conduit member are unitary.

4. The device as defined in claim 1 constructed of a liquid imperforate material.

5. The device as defined in claim 1 wherein said recesses are approximately 180° apart on said collar.

6. The device as defined in claim 1 wherein said end portions are substantially perpendicular to said arm.

7. The device as defined in claim 1 wherein said arms are adapted to pivot relative to said second collar, said arms being disposed approximately 180° apart.

8. The device as defined in claim 1 in combination with a container having a mouth portion and external threads therearound.